(12) United States Patent
Grinberg

(10) Patent No.: US 11,607,180 B2
(45) Date of Patent: Mar. 21, 2023

(54) COMPUTER-IMPLEMENTED METHOD AND A PORTABLE DEVICE FOR ANALYZING GLUCOSE MONITORING DATA INDICATIVE OF A GLUCOSE LEVEL IN A BODILY FLUID, AND A COMPUTER PROGRAM PRODUCT

(71) Applicant: Roche Diabetes Care, Inc., Indianapolis, IN (US)

(72) Inventor: Itzhak Grinberg, Haifa (IL)

(73) Assignee: ROCHE DIABETES CARE, INC., Indianapolis, IN (US)

(*) Notice: Subject to any disclaimer, the term of this patent is extended or adjusted under 35 U.S.C. 154(b) by 120 days.

(21) Appl. No.: 16/484,875

(22) PCT Filed: Feb. 14, 2018

(86) PCT No.: PCT/EP2018/053669
§ 371 (c)(1),
(2) Date: Aug. 9, 2019

(87) PCT Pub. No.: WO2018/149872
PCT Pub. Date: Aug. 23, 2018

(65) Prior Publication Data
US 2020/0069258 A1 Mar. 5, 2020

(30) Foreign Application Priority Data
Feb. 14, 2017 (EP) .................... 17155983

(51) Int. Cl.
*A61B 5/00* (2006.01)
*G16H 15/00* (2018.01)
(Continued)

(52) U.S. Cl.
CPC ........ *A61B 5/7282* (2013.01); *A61B 5/14532* (2013.01); *A61B 5/681* (2013.01);
(Continued)

(58) Field of Classification Search
CPC ..... A61B 5/14532; A61B 5/72; A61B 5/7271; A61B 5/7282; A61B 5/742–743;
(Continued)

(56) References Cited

U.S. PATENT DOCUMENTS 8,206,296 B2 * 6/2012 Jennewine ........... A61B 5/7275
600/347
9,033,877 B2 * 5/2015 Werner ................. A61B 5/743
600/365
(Continued)

FOREIGN PATENT DOCUMENTS

WO WO-2011026053 A1 * 3/2011 ......... A61B 5/14532
WO WO-2012108938 A1 * 8/2012 ............. G16H 20/00
(Continued)

OTHER PUBLICATIONS

Office Action in related RU 2019125313 dated Oct. 5, 2020.

*Primary Examiner* — Navin Natnithithadha
*Assistant Examiner* — Alice Ling Zou
(74) *Attorney, Agent, or Firm* — Woodard, Emhardt, Henry, Reeves & Wagner, LLP

(57) ABSTRACT

A computer-implemented method for analyzing glucose monitoring data comprising: receiving first glucose monitoring data indicative of a glucose level at a measurement time, the first glucose monitoring signals detected in one or more glucose measurement time periods over a first monitoring time period of a continuous glucose monitoring, determining at least one first range event selected from the following group: a normal glucose level event, a hyperglycaemia event, or a hypoglycaemia event; determining how often the first range event is determined for the first monitoring time period; providing a first minimum total, measurement time period, the first minimum total measurement time period being shorter in time than the first monitoring time period; generating first display data representing, for
(Continued)

Figure 1:
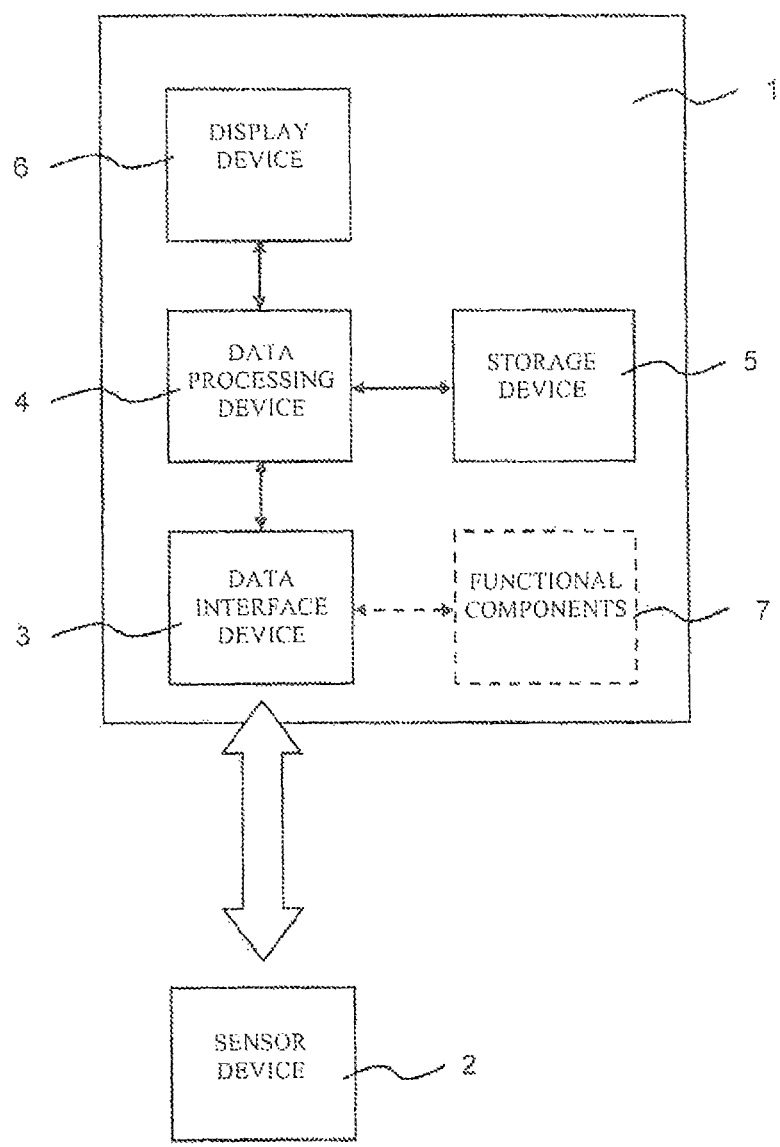

the at least one first range event, the number of first range events in a graphical representation, if the one or more glucose measurement time periods sum up to at least a first minimum total measurement time period; and outputting the first display data through the display device. Further, a portable device and a non-transitory computer readable medium are provided.

27 Claims, 3 Drawing Sheets

(51) Int. Cl.
G16H 40/63 (2018.01)
A61B 5/145 (2006.01)

(52) U.S. Cl.
CPC ............ *A61B 5/6898* (2013.01); *A61B 5/743* (2013.01); *G16H 15/00* (2018.01); *G16H 40/63* (2018.01); *A61B 2560/0431* (2013.01)

(58) Field of Classification Search
CPC .............. A61B 5/14503; A61B 5/1451; A61B 5/14865; A61B 5/7221; A61B 2560/0431; G16H 50/20; G16H 15/00; G16H 40/63; G16H 50/30; G16H 10/60; G16H 40/60–67
See application file for complete search history.

(56) References Cited

U.S. PATENT DOCUMENTS

| 2006/0253067 | A1* | 11/2006 | Staib ..................... G01N 33/66 604/67 |
| 2008/0071580 | A1* | 3/2008 | Marcus .................. G16H 15/00 705/3 |
| 2010/0056993 | A1* | 3/2010 | Chase ............... A61M 5/14276 604/66 |
| 2012/0059673 | A1 | 3/2012 | Cohen et al. |
| 2013/0035871 | A1* | 2/2013 | Mayou ................... G16H 50/20 702/26 |
| 2013/0090088 | A1 | 4/2013 | Chevsky et al. |
| 2013/0246096 | A1* | 9/2013 | Koehler ................. G16H 10/40 705/3 |
| 2014/0088393 | A1 | 3/2014 | Bernstein et al. |
| 2014/0200426 | A1* | 7/2014 | Taub ................... A61B 5/14532 600/347 |
| 2015/0207796 | A1* | 7/2015 | Love ....................... H04L 63/10 726/4 |
| 2016/0328991 | A1* | 11/2016 | Simpson ............ G09B 19/0092 |
| 2017/0147769 | A1* | 5/2017 | Bernstein ........... A61B 5/14546 |

FOREIGN PATENT DOCUMENTS

| WO | WO-2014145335 A1 * | 9/2014 | ............ G06F 19/00 |
| WO | WO-2018115317 A1 * | 6/2018 | ............ G16H 10/65 |
| WO | WO-2018178942 A1 * | 10/2018 | |

* cited by examiner

COMPUTER-IMPLEMENTED METHOD AND A PORTABLE DEVICE FOR ANALYZING GLUCOSE MONITORING DATA INDICATIVE OF A GLUCOSE LEVEL IN A BODILY FLUID, AND A COMPUTER PROGRAM PRODUCT

The present disclosure relates to computer-implemented method and a portable device for analyzing glucose monitoring data indicative of a glucose level in a bodily fluid, and a computer program product.

BACKGROUND

Glucose monitoring helps people with diabetes manage the disease and avoid its associated problems. A person can use the results of glucose monitoring to make decisions about food, physical activity, and medications. A common way to check glucose level is performing discontinuous monitoring. Such checking usually involves pricking a fingertip with an automatic lancing device to obtain a blood sample and then using a glucose meter to measure the blood sample's glucose level. Such monitoring may also be referred to as spot monitoring.

As an alternative or in addition continuous glucose monitoring (CGM) may be applied. A system for CGM may use a body sensor inserted under the skin to check glucose levels. The sensor stays in place for several days to weeks and then must be replaced. A transmitter sends information about an analyte value or level indicative of the glucose level (e.g., via wireless data transmission) from the sensor to a monitor device. The user may check blood samples with a glucose meter to calibrate the devices.

Patients with diabetes may be asked to perform a number of collections in an effort to diagnose a chronic diabetic condition (DC) or to optimize therapy. For example, diabetic patients may measure their glucose level concurrently with various events that occur according to the patient's lifestyle. The events may or may not be correlated with or influence biomarkers of the chronic DC or the optimization or therapy. However, the correlations between the events in the biomarkers of the chronic DC can be difficult to identify. Methods and systems were proposed for visualizing correlations between glucose data and events.

Document US 2012/059673 A1 refers to a diabetes management system which selects variable threshold parameters that are utilized in a report. A first low threshold glucose reading and a first high threshold glucose reading for a before meal event timeframe are selected. A second low threshold glucose reading and a second high threshold high glucose reading are selected for an after meal event timeframe. The threshold readings are stored in a database. The diabetes data management system analyzes glucose behavior around meal events. The system receives a plurality of glucose readings for a time period, receives a first time range as a pre-meal analysis period for the first meal event and receives a second time range as a post-meal analysis period for the first meal event. The system creates a graph which highlights the pre-meal analysis period, the post-meal analysis period, and displays the plurality of glucose readings for the time period.

SUMMARY

It is an object to provide improved technologies for analyzing glucose monitoring data indicative of a glucose level in a bodily fluid. According to an object, non-correct analysis of glucose monitoring signals shall be avoided.

According to a further object, the technologies shall provided for a simple and efficient way for analyzing continuous, quasi-real time monitoring data to provide the user with condensed information for giving a simple and effective indication on the glycemic status of the user.

A computer-implemented method for analyzing glucose monitoring data indicative of a glucose level in a bodily fluid is provided according to claim 1. Further, a portable device for analyzing glucose monitoring data indicative of a glucose level in a bodily fluid is provided and a non-transitory computer readable medium according to claims 13 and 14, respectively, are provided. Alternative embodiments are disclosed in dependent claims.

According to an aspect, a computer-implemented method for analyzing glucose monitoring data indicative of a glucose level in a bodily fluid is provided. The method, in a data processing device provided with one or more processors and connected to a display device, is comprising: receiving first glucose monitoring data representing a plurality of first glucose monitoring signals each indicative of a glucose level in a bodily fluid at a measurement time, the first glucose monitoring signals detected in one or more glucose measurement time periods over a first monitoring time period of a continuous glucose monitoring the first monitoring time period being less than or equal to 24 hours; and determining, from the first glucose monitoring data, first range events comprising at least one first range event selected from the following group:

- a normal glucose level event which is determined, if the first glucose monitoring signals are indicating a glucose level within a glucose level target range including an upper and a lower target limit of the glucose level target range;
- a hyperglycaemia event which is determined, if the first glucose monitoring signals are indicating a glucose level above an upper glucose level limit, which is greater than the upper target limit; and
- a hypoglycaemia event which is determined, if the first glucose monitoring signals are indicating a glucose level below a lower glucose level limit, which is lower than the lower target limit.

The method is further comprising: determining, for the at least one first range event, a number of first range events indicating how often the at least one first range event is determined for the first monitoring time period; providing a first minimum total measurement time period, the first minimum total measurement time period being shorter in time than the first monitoring time period; generating first display data representing, for the at least one first range event, the number of first range events in a graphical representation, if the one or more glucose measurement time periods sum up to at least the first minimum total measurement time period; and outputting the first display data through the display device.

According to a further aspect, a portable device for analyzing glucose monitoring data indicative of a glucose level in a bodily fluid is provided. The portable device comprises a data processing device provided with one or more processors and a display device. The data processing device is configured for: receiving first glucose monitoring data representing a plurality of first glucose monitoring signals each indicative of a glucose level in a bodily fluid at a measurement time, the first glucose monitoring signals detected in one or more glucose measurement time periods over a first monitoring time period of a continuous glucose monitoring the first monitoring time period being less than or equal to 24 hours; and determining, from the first glucose monitoring data, first range events comprising at least one first range event selected from the following group:

a normal glucose level event which is determined, if the first glucose monitoring signals are indicating a glucose level within a glucose level target range including an upper and a lower target limit of the glucose level target range;

a hyperglycaemia event which is determined, if the first glucose monitoring signals are indicating a glucose level above an upper glucose level limit, which is greater than the upper target limit; and a hypoglycaemia event which is determined, if the first glucose monitoring signals are indicating a glucose level below a lower glucose level limit, which is lower than the lower target limit.

The data processing device is further configured for the following: determining, for the at least one first range event, a number of first range events indicating how often the at least one first range event is determined for first monitoring time period; providing a first minimum total measurement time period, the first minimum total measurement time period being shorter in time than the first monitoring time period; and generating first display data representing, for the at least one first range event, the number of first range events in a graphical representation, if the one or more glucose measurement time periods sum up to at least the first minimum total measurement time period; and outputting the first display data through the display device.

Another aspect refers to a computer program product, preferably stored on a storage medium and configured to perform a method for analyzing glucose monitoring data indicative of a glucose level during operation on a portable device.

According to the aspects of the disclosure, continuous, quasi-real time monitoring data can be analyzed in a simple and efficient way to provide the user with condensed information for giving a simple and effective indication on the glycemic status of the user. Additionally, the simple and efficient analysis allows functioning as a motivational tool to the user, since the user can easily distinguish between good and bad glycemic control on a daily basis.

The method may further comprise the following: determining, from the first glucose monitoring data, first range events comprising a plurality of first range events; determining, for each of the plurality of first range events, the number of first range events indicating how often each of the plurality of first range events is determined for first monitoring time period; and displaying, for each of the plurality of first range events, the number of first range events in the graphical representation, if the one or more glucose measurement time periods sum up to at least the first minimum total measurement time period.

The generating of the first display data may comprise generating first display data representing, for the at least one first range event or each of the plurality of first range events, the number of first range events in a graphical bar representation.

The generating of the first display data may comprise generating first display data representing, for the at least one first range event or each of the plurality of first range events, the number of first range events in a graphical single element representation, for example, a graphical single bar representation.

The generating may comprise generating the first display data, if the one or more glucose measurement time periods sum up to at least two hours or eighteen hours. The first minimum total measurement time period may be greater than 5 minutes and less than 24. In further embodiments, the first minimum total measurement time period may be greater than 2 hours, 5 hours, 8 hours, 10 hours, 12 hours, 14 hours or 18 hours to allow for sufficient statistics on the number of first range events determination.

The monitoring time period may comprise a period of 24 hours. The first monitoring time period may determine a day period. The graphical representation may be representing a day summary. The first monitoring time period may correspond to a 24 hour period representing a day period assigned to a date The method may further comprise the following:

receiving second glucose monitoring data representing one or more of second glucose monitoring signals each corresponding to a blood glucose level measured in a blood sample at a measurement time, the one or more second glucose monitoring signals detected at one or more points in time in a second monitoring time period of a blood glucose monitoring, the second monitoring time period being less than or equal to 24 hours;

determining, from the second glucose monitoring data, second range events comprising at least one second range event selected from the following group:

a hyperglycaemia event which is determined, if the first glucose monitoring signals are indicating a glucose level above an upper glucose level limit, which is greater than the upper target limit; and a hypoglycaemia event which is determined, if the first glucose monitoring signals are indicating a glucose level below a lower glucose level limit, which is lower than the lower target limit;

determining, for the at least one second range event, a number of second range events indicating, how often the at least one second range event is determined for the second monitoring time period;

generating second display data representing, for the at least one second range event, the number of second range events in a further graphical representation; and outputting the second display data through the display device, if the one or more glucose measurement time periods, in which the first glucose monitoring signals are detected, do not sum up to at least the first minimum total measurement time period.

The further graphical representation may be a graphical non-bar representation. In general, the second display data may be representing a further graphical element different from a graphical element provided by the first display data.

The method may further comprise providing a minimum range event time period indicating a time period required for the at least one first range event and/or at least one second range event to be determined as one of the range events; and determining, from the first/second glucose monitoring data, the at least one first/second range event, if the at least one first/second range event is matching the minimum range event time period. For example, the minimum range event time period may be five minutes, thereby, defining that a range event is only displayed if the range event is determined to be present in the glucose monitoring signals for at least five minutes. In the graphical representation, the minimum range event time period may be represented by a minimum graphical element length, for example, a minimum relative sub-element length such as five percent or ten percent of the total graphical element length displayed. In case of a graphical bar representation, the minimum range event time period may be represented by a minimum bar element length, for example, a minimum relative sub-bar length such as five percent or ten percent of the total bar length displayed.

The group of first range events may further comprise an intermediate low event which is determined, if the first glucose monitoring signals are indicating a glucose level above the lower glucose level limit and below the upper target limit.

First display data sets each may be representing, for the at least one first range event or each of the plurality of first range events, the number of first range events in a graphical representation, if the one or more glucose measurement time periods sum up to at least the first minimum total measurement time period, wherein each of the first display data sets is based on first glucose monitoring data within the first monitoring time period representing a day period assigned to a date and wherein the first display data sets are outputted through the display device. The graphical representation may be a graphical bar representation.

The second display data sets each may be representing, for the at least one second range event or each of the plurality of second range events, the number of second range events in a further graphical representation, wherein each of the second display data sets is based on second glucose monitoring data within the second monitoring time period representing a day period assigned to a date and wherein the second display data sets are outputted through the display device. The further graphical representation may be a graphical non-bar representation.

For the first and second display data sets, each data set may be representing a day period assigned to a date, wherein the first and second display data sets are outputted through the display device.

The determining, from the first glucose monitoring data, of first range events, and the determining from the first glucose monitoring data a number of first range events indicating how often the at least one first range event is determined for the first monitoring time period, and the generating first display data representing the number of first range events in the graphical representation, if the one or more glucose measurement time periods sum up to at least the first minimum total measurement time period, may be performed and updated whenever first glucose monitoring data measured continuously, in real-time is received within the first time period. The graphical representation may be a graphical bar representation.

The method may further comprise the following: determining that, for the first glucose monitoring data, the one or more glucose measurement time periods sum up to at least the first minimum total measurement time period within the first monitoring time period representing a day period assigned to a date; and displaying, together with date display data representing the date, third display data on the display device, the third display data indicating that, for the day period assigned to the date, the one or more glucose measurement time periods sum up to at least the first minimum total measurement time period. The date display data may be indicating a numerical representation of the date. The third display data may comprise or may be represented by a graphical element displayed in the proximity of the numerical representation of the date on the display device. For example, another graphical bar or a graphical line may be displayed, such as a grey bar or line. Alternative graphical elements may be applied.

The sensor used in the continuous glucose monitoring (CGM) may be a disposable sensor which may also referred to as single use sensor. The body worn sensor may be a sensor for collecting in vivo sensor data. The body worn sensor may be a subcutaneous sensor for measuring the glucose level in interstitial fluid.

The glucose monitoring may be performed by a medical monitoring system provided as a CGM system.

The portable device may receive the continuous monitoring data from a body worn sensor via a wireless connection. Interface devices or modules for such wireless communication may be operable under the Bluetooth, in particular the Bluetooth Low Energy Standard. For initiation or starting of the sensor session, the sensor may be inserted subcutaneously. Then the portable device and the body worn sensor unit are paired (specifically, at least exchange of ID information).

The body worn sensor may be a sensor for collecting in vivo sensor data. The body worn sensor may be a continuous monitoring sensor, specifically a continuous glucose monitoring sensor configured to be provided in the interstitium. With regard to a glucose measurement or monitoring, a glucose level or value may be determined by analyzing a blood sample via continuous glucose monitoring via a fully or partially implanted sensor. In general, in the context of CGM a glucose value or level in a bodily fluid may be determined. The analyte value may be, e.g., subcutaneously measured in an interstitial fluid. CGM may be implemented as a nearly real-time or quasi-continuous monitoring procedure frequently or automatically providing/updating analyte values without user interaction.

The display device may be provided in the portable device. As an alternative, the display device may be provided separately from the portable device. For outputting the video data may be transmitted from the portable device to the separated display device via a wireless or a wired data transmission connection.

The portable device may be selected from the following group of portable devices: mobile phone, tablet computer, laptop computer, portable medical device, portable medical measurement device, and a smart watch. The portable device may be configured with a software program being downloaded from the internet, for example, in form of a so-called App.

DESCRIPTION OF FURTHER EMBODIMENTS

Figure 2:
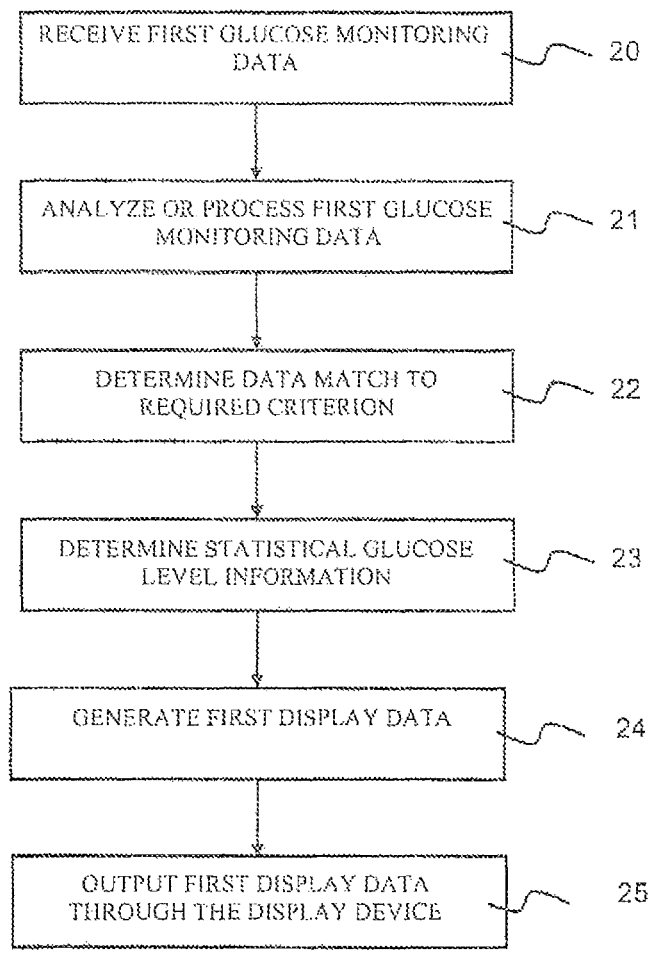
Figure 3:
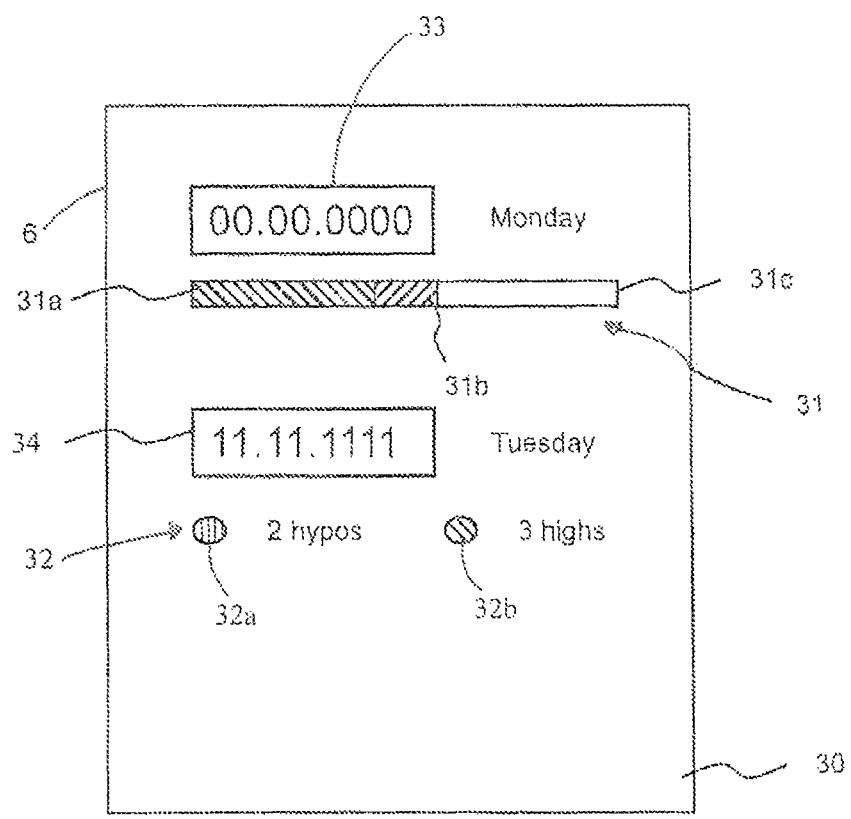

Following, embodiments, by way of example, are described with reference to figures. In the figures show:

FIG. 1 a schematic representation of an arrangement with a portable device and a sensor device to be worn on a body;

FIG. 2 a schematic representation for a method for analyzing glucose monitoring data indicative of a glucose level in a bodily fluid; and FIG. 3 a schematic representation of a window on a display representing output of different graphical data.

FIG. 1 shows a schematic representation of an arrangement with a portable device 1 and a sensor device 2 provided with a sensor to be worn by a patient. The sensor device 2 is configured for continuous glucose monitoring. The portable device is provided with a data interface device 3, a data processing device 4, a storage device 5, and a display device 6. The data processing device 4, at least for unidirectional data transmission, is connected to the data interface device 3, the storage device 5, and the display device 6. Further functional components 7 may be provided.

The data processing device 4 may comprise one or more processors.

Data transmission between the portable device 1 and the sensor device 2 may be provided by wireless and/or wired data transmission. Typically the portable device 1 receives data from the body worn sensor device 2 via a wireless connection. Preferred interfaces for such wireless communication are operable under Bluetooth or Bluetooth Low Energy Standard. On initiation of the sensor session, the portable device 1 and the body worn sensor device 2 are paired (specifically, exchange of ID information) and during the sensor session the body worn sensor device 2 may constantly transmit raw or preprocessed monitoring data to the portable device 1, where it may be either stored and displayed or only stored and not displayed.

The portable device 1 may be selected from the following group of portable devices: mobile phone, tablet computer, laptop computer, portable medical device, portable medical measurement device, and a smart watch. The portable device may be configured with a software program being downloaded from the internet, for example, in form of a so-called App.

FIG. 2 shows a schematic representation for a method for analyzing glucose monitoring data indicative of a glucose level in a bodily fluid in the portable device 1.

In step 20, a stream of first glucose monitoring data is received in the portable device 1. According to the embodiment shown, the first glucose monitoring data are received from the sensor device 2. The first glucose monitoring data are representing a plurality of first glucose monitoring signals each indicative of a glucose level in a bodily fluid at a measurement time. The first glucose monitoring signals are detected in one or more glucose measurement time periods over a first monitoring time period of a continuous glucose monitoring, for example, by the sensor device 2. For example, the first glucose monitoring signals may represent the result of a continuous glucose monitoring for a patient over several hours, such as 12 or 18 hours, or one or more days. Specifically, a time period of 24 hours such as a day or day period may be of interest for the patient or user.

In step 21, in the portable device 1 the stream of first glucose monitoring data is analyzed or processed.

According to step 22, it is determined whether the first glucose monitoring data match at least one required criterion. In an alternative, a first minimum total measurement time period is provided, the first minimum total measurement time period being shorter in time than the first monitoring time period. It is checked whether the one or more glucose measurement time periods sum up to at least the first minimum total measurement time period.

If the first glucose monitoring data match the at least one required or checked criterion, for the first glucose monitoring data, in step 23, statistical glucose level information is determined by applying a statistical analysis to the first glucose monitoring data. For example, by the statistical analysis it may be determined a relative value with regard to the first monitoring time period for how long at least one of the following events is observed for the first glucose monitoring signals: the first glucose monitoring signals indicate a glucose level within a glucose level target range; the first glucose monitoring signals indicate a high glucose level above an upper glucose level limit (hyperglycaemia event); and the first glucose monitoring signals indicate a low glucose level below a lower glucose level limit (hypoglycaemia event). For example, for a glucose monitoring period of 24 hours the following may be determined: 30 percent of the time period there was a high glucose level; 10 percent of the monitoring time period there was a low glucose level, and for 60 percent of the monitoring time period there was a glucose level within the glucose level target range ("normal"). Such relative values regarding the monitoring time may be presented by sub-bar elements in a bar representation (see, for example, FIG. 3). Alternative graphical elements and sub-elements may be applied. For example, a circle chart may be applied.

In step 24, first display data are generated which are indicative of the statistical information determined before. The first display data are outputted through the display device 6 in step 25. For example, the statistical information may be represented by a continuous bar on the display device 6, where the continuous bar representation comprises a plurality of sub-sections or sub-bar elements, e.g. three continuous sub-sections (with different color or different shading) representing the high glucose level, the low glucose level, and the normal glucose level, respectively. An example for such graphical output is shown in FIG. 3.

At least one of the determining of the statistical glucose level information and the generating of the first display data may be only be performed if the first glucose monitoring data match the at least one required criterion. For example, the one or more glucose measurement time periods shall sum up to at least the first minimum total measurement time period.

In an alternative embodiment, second glucose monitoring data may be received in the portable device 1. The second glucose monitoring data are representing a plurality of second glucose monitoring signals each indicative of a blood glucose level at a measurement time point. The second glucose monitoring signals are detected in the blood glucose monitoring being a different type of glucose monitoring as the one for detecting the first glucose monitoring signals. The second glucose monitoring may be a non-continuous (sometimes also referred to as spot-monitoring) or a continuous glucose monitoring.

The second blood glucose monitoring is performed over a second monitoring time period. Following, for the second glucose monitoring data it is determined that such second blood glucose monitoring data are not matching the at least one required criterion. For example, one or more glucose measurement time periods do not sum up to at least a second minimum total measurement time period provided for the second glucose monitoring analysis. The second minimum total measurement time may be equal to or different from the first minimum total measurement time.

In response, for the second blood glucose monitoring data non-statistical glucose level information is determined by applying a non-statistical analysis to the second blood glucose monitoring data. For example, such non-statistical analysis may comprise determining a number for at least one of the low glucose level, the high glucose level, and the normal glucose level within the second glucose monitoring time period. Second display data are generated, the second display data being indicative of the non-statistical information. Following, the second display data are outputted through the display device 6. An example for the second display data is also shown in FIG. 3.

FIG. 3 shows a schematic representation of a window 30 on a display, for example on the display device 6, representing output of the first and second display data determined as outlined above. The first display data is displayed by a continuous graphical bar element 31 having graphical sub-bar elements 31a, . . . , 31c.

The second display data is represented by two separated graphical non-bar elements 32 such as dots 32a, 32b. The dots 32a, 32b each represent a number of range events, namely hypoglycaemia events and hyperglycaemia events.

The first and second display data represented by the graphical elements 31, 32 refer to a graphical representation of the result of an analysis of the glucose monitoring signals gathered for two different days (two different glucose monitoring periods). The different days are represented by numerical date information 33, 34. While for the first day (see graphical bar element 31, Monday) the glucose monitoring signals are fulfilling the requirements for the graphical bar representation, since, for example, the one or more glucose measurement time periods sum up to at least the first minimum total measurement time period. This is not the case for a glucose monitoring signals detected for the second day (Tuesday). Therefore, in response to determining that the glucose monitoring data provided for the second day are not matching the requirement, only the non-bar elements 31, 32 are generated and outputted via the display device 6.

The invention claimed is:

1. A method for operating a glucose monitoring and display system for a patient, including determining and analyzing glucose monitoring data of the patient indicative of a glucose level in a bodily fluid, comprising:
   using a glucose sensor, collecting first glucose monitoring data comprising a plurality of first glucose monitoring signals for a first monitoring time period;
   transmitting the first glucose monitoring data from the glucose sensor to a data processing device provided with one or more processors and connected to a display device;
   receiving in the data processing device the first glucose monitoring data, the first glucose monitoring data representing the plurality of first glucose monitoring signals each indicative of a glucose level in a bodily fluid at a measurement time, the first glucose monitoring signals detected in one or more first glucose measurement time periods over the first monitoring time period, the first monitoring time period being less than or equal to 24 hours;
   using the data processing device, determining, from the first glucose monitoring data, first range events comprising at least one first type range event selected from the group consisting of:
      a normal glucose level event, which is determined if the first glucose monitoring signals are indicating a glucose level within a glucose level target range including an upper and a lower target limit of the glucose level target range;
      a hyperglycaemia event, which is determined if the first glucose monitoring signals are indicating a glucose level above an upper glucose level limit, which is greater than the upper target limit; and
      a hypoglycaemia event, which is determined if the first glucose monitoring signals are indicating a glucose level below a lower glucose level limit, which is lower than the lower target limit;
   determining, for the at least one first type range event, the number of the at least one first type range events indicating how often the at least one first type range event is determined for the first monitoring time period;
   providing a first minimum total measurement time period corresponding to the first type range event and being shorter in time than the first monitoring time period;
   using the data processing device, determining a sum of the first glucose measurement time periods,
   if the sum is more than the first minimum total measurement time period then, using the data processing device and the display device, generating first display data representing the number of first type range events in a first graphical representation and outputting the first display data through the display device as a first graphical display, and
   if the sum is less than the first minimum total measurement time period, then, using the data processing device and the display device, generating first display data representing the number of first type range events in a second graphical representation and outputting the first display data through the display device as a second graphical display.

2. The method according to claim 1, further comprising determining, from the first glucose monitoring data, a plurality of types of first range events, each of the plurality of types of first range events having a correlated first minimum total measurement time period;
   determining, for each of the plurality of types of first range events, the number of first type range events indicating how often each of the plurality of first type range events is determined for the first monitoring time period; and
   displaying, for each of the plurality of first type range events, the number of first type range events in the first graphical representation, if the one or more glucose measurement time periods sum up to at least the correlated first minimum total measurement time period.

3. The method according to claim 2, wherein the generating of the first display data in the first graphical representation comprises generating first display data representing, for each of the plurality of first type range events, the number of first type range events in a single graphical element representation.

4. The method according to claim 2, wherein, if the one or more glucose measurement time periods sum up to at least the first minimum total measurement time period, then the first display data comprises first display data sets each representing, for the at least one first type range event or each of the plurality of first type range events, the number of first type range events in the first graphical representation, if the one or more glucose measurement time periods sum up to at least the first minimum total measurement time period, wherein each of the first display data sets is based on first glucose monitoring data within the first monitoring time period representing a day period assigned to a date and wherein the first display data sets are outputted through the display device.

5. The method according to claim 1, wherein the first minimum total measurement time period is greater than 5 minutes and less than 24 hours.

6. The method according to claim 1, wherein the first monitoring time period corresponds to a 24 hour period representing a day period assigned to a date.

7. The method according to claim 1, further comprising:
   receiving second glucose monitoring data representing one or more second glucose monitoring signals each corresponding to a blood glucose level measured in a blood sample of the patient at a measurement time, the one or more second glucose monitoring signals detected at one or more points during a second monitoring time period of a blood glucose monitoring system, the second monitoring time period being less than or equal to 24 hours;
   using the data processing device determining, from the second glucose monitoring data, second range events comprising at least one second type range event selected from the group consisting of:

a hyperglycaemia, event which is determined if the second glucose monitoring signals are indicating a glucose level above an upper glucose level limit, which is greater than an upper target limit; and a hypoglycaemia event, which is determined if the second glucose monitoring signals are indicating a glucose level below a lower glucose level limit, which is lower than a lower target limit;

determining, for the at least one second type range event, the number of the at least one second type range events indicating how often the at least one second type range event is determined for the second monitoring time period;

providing a second minimum total measurement time period, the second minimum total measurement time period being shorter than the second monitoring time period;

using the data processing device, determining a second sum of the second glucose measurement time periods for the second glucose monitoring data, and if the second sum is more than the second minimum total measurement time period, then, using the data processing device and the display device, generating second display data representing the number of second type range events in a third graphical representation and outputting the second display data through the display device as a third graphical display, and if the second sum is less than the second minimum total measurement time period, then, using the data processing device and the display device, generating second display data representing the number of second type range events in a fourth graphical representation and outputting the second display data through the display device as a fourth graphical display.

8. The method according to claim 7, further comprising providing a minimum range event time period indicating a time period required for at least one of the at least one first type range event and the at least one second type range event to be determined as one of the range events; and determining the at least one first or second range event from the first or second glucose monitoring data, if a time period of the at least one first or second range event is matching or exceeding the minimum range event time period.

9. The method according to claim 7, further comprising at least one of:

determining that, for the first glucose monitoring data, the one or more glucose measurement time periods sum up to at least the first minimum total measurement time period within the first monitoring time period representing a day period assigned to a date; and displaying, together with date display data representing the date, third display data on the display device, the third display data indicating that, for the day period assigned to the date, the one or more glucose measurement time periods sum up to at least the first minimum total measurement time period.

10. The method according to claim 7 wherein the second display data comprises second display data sets each representing, for the at least one second type range event or each of the second type range events, the number of second type range events in the third or fourth graphical representation, wherein each of the second display data sets is based on second glucose monitoring data within the second monitoring time period representing a day period assigned to a date and wherein the second display data sets are outputted through the display device.

11. The method according to claim 7, further comprising determining, from the first glucose monitoring data, a plurality of first type range events;

determining, for each of the plurality of first type range events, the number of first type range events indicating how often each of the plurality of first type range events is determined for the first monitoring time period; and displaying, for each of the plurality of first type range events, the number of first type range events in the first graphical representation, if the one or more glucose measurement time periods sum up to at least the first minimum total measurement time period.

12. The method according to claim 11, wherein if the one or more glucose measurement time periods sum up to at least the first minimum total measurement time period, then the first display data comprises first display data sets each representing, for the at least one first type range event or each of the plurality of first type range events, the number of first type range events in the first graphical representation, wherein each of the first display data sets is based on first glucose monitoring data within the first monitoring time period representing a day period assigned to a date and wherein the first display data sets are outputted through the display device.

13. The method according to claim 12 wherein the second display data comprises second display data sets each representing, for the at least one second type range event or each of the plurality of second type range events, the number of second type range events in the third or fourth graphical representation, wherein each of the second display data sets is based on second glucose monitoring data within the second monitoring time period representing a day period assigned to a date and wherein the second display data sets are outputted through the display device.

14. The method of claim 7 in which the first graphical representation comprises a bar graph showing the first type range events as sub-bar elements.

15. The method according to claim 1, wherein the group of first range events further comprises an intermediate low event which is determined if the first glucose monitoring signals are indicating a glucose level above the lower glucose level limit and below the lower target limit.

16. The method according to claim 1, further comprising performing and updating, whenever first glucose monitoring data measured continuously in real-time is received within the first time period, the following:

determining, from the first glucose monitoring data, the first type range events;

determining, from the first glucose monitoring data, the number of first type range events indicating how often the at least one first type range event is determined for the first monitoring time period; and generating the first display data representing the number of first type range events in the first graphical representation, if the one or more glucose measurement time periods sum up to at least the first minimum total measurement time period.

17. A non-transitory computer readable medium storing a program causing, when loaded to a data processing device having one or more processors and connected to a display device, the data processing device to perform the method of claim 1.

18. The method of claim 1 in which the first graphical representation comprises a bar graph showing the first type range events as sub-bar elements.

19. The method of claim 18 in which the bar graph comprises sub-bar elements representing a normal glucose level event, a hyperglycemia event, and a hypoglycemia event.

20. The method of claim 1 in which the first graphical representation comprises a circle chart.

21. A portable device for determining and displaying glucose monitoring data indicative of a glucose level in a bodily fluid of a patient, the device comprising:
   a data processing device provided with one or more processors; and
   a display device,
   the data processing device being configured for
      receiving from a glucose monitoring system first glucose monitoring data representing a plurality of first glucose monitoring signals each indicative of a glucose level in a bodily fluid at a measurement time, the first glucose monitoring signals detected in one or more first glucose measurement time periods over a first monitoring time period of a glucose monitoring system, the first monitoring time period being less than or equal to 24 hours;
      converting the first glucose monitoring data to first range events comprising at least one first type range event selected from the group consisting of:
         a normal glucose level event, which is determined if the first glucose monitoring signals are indicating a glucose level within a glucose level target range including an upper and a lower target limit of the glucose level target range;
         a hyperglycaemia event, which is determined if the first glucose monitoring signals are indicating a glucose level above an upper glucose level limit, which is greater than the upper target limit; and
         a hypoglycaemia event, which is determined if the first glucose monitoring signals are indicating a glucose level below a lower glucose level limit, which is lower than the lower target limit;
      determining, for the at least one first type range event, the number of first type range events indicating how often the at least one first type range event is determined for the first monitoring time period;
      providing a first minimum total measurement time period corresponding to the first type range events and being shorter in time than the first monitoring time period;
      using the data processing device, determining the sum of the first glucose measurement time periods, and
      if the sum is more than the first minimum total measurement time period, generating first display data representing, for the at least one first type range event, the number of first type range events in a first graphical representation; and outputting the first display data through the display device as a first graphical display;
      if the sum is less than the first minimum total measurement time period, then, generating first display data representing, for the at least one first type range event, the number of first type range events in a second graphical representation; and outputting the first display data through the display device as a second graphical display.

22. The portable device of claim 21 in which the first graphical representation comprises a bar graph showing the first type range events as sub-bar elements.

23. A method for operating a glucose monitoring system comprising a subcutaneous, body worn sensor for collecting continuous monitoring data relating to a glucose level in interstitial fluid of a patient, the method comprising:
   using the subcutaneous sensor, collecting glucose monitoring data comprising a plurality of glucose monitoring signals of a patient detected in one or more first glucose measurement time periods over a first monitoring time period;
   transmitting the continuous monitoring data from the subcutaneous sensor to a portable device;
   using the portable device, converting the glucose monitoring signals to corresponding types of glucose range events selected from the group consisting of normal glucose events, hyperglycaemia events, and hypoglycaemia events;
   selecting a first type of glucose range event;
   determining the number of the first type of glucose range events during the first monitoring time period;
   using the portable device, determining a sum of the first glucose measurement time periods, and
   if the sum is more than a first minimum total measurement time corresponding to the first type of glucose range events, then using the portable device, generating and displaying the first type of glucose range events using a first graphical representation, and
   if the sum is not more than the first minimum total measurement time, then using the portable device, generating and displaying the first type of glucose range events using a second graphical representation.

24. The method of claim 23 and further comprising:
   selecting a second type of glucose range event;
   determining the number of the second type of glucose range events detected in one or more second glucose measurement time periods during a second monitoring time period;
   using the portable device, determining if the sum of the second glucose measurement time periods is more than a second minimum total measurement time corresponding to the second type of glucose range events; and
   if so, then using the portable device, generating and displaying the second type of glucose range events using the first graphical representation; and
   if not, then using the portable device, generating and displaying the second type of glucose range events using the second graphical representation.

25. The method of claim 24 in which the second monitoring time period comprises one or more second glucose measurement time periods which may be the same as or different from the first glucose measurement time periods.

26. The method of claim 24 and further comprising:
   selecting a third type of glucose range event;
   determining the number of the third type of glucose range events during a third monitoring time period;
   using the portable device, determining if the third monitoring time period is more than a third minimum total measurement time corresponding to the third type of glucose range event; and
   if the third monitoring time period exceeds the third minimum total measurement time, then, using the portable device, generating and displaying the third type of glucose range events using the first graphical representation; and if the third monitoring time period does not exceed the third minimum total measurement time, then, using the portable device, generating and displaying the third type of glucose range events using the second graphical representation.

27. The method of claim 23 in which the first graphical representation comprises a bar graph showing the first type range events as sub-bar elements.

\* \* \* \* \*